US00PP13650P29

(12) United States Plant Patent
Verwer

(10) Patent No.: US PP13,650 P2
(45) Date of Patent: Mar. 11, 2003

(54) DAHLIA PLANT NAMED 'KARMA CORONA'

(75) Inventor: Aad W. M. Verwer, Lisse (NL)

(73) Assignee: Gebr. Verwer, Lisse (NL)

( * ) Notice: Subject to any disclaimer, the term of this patent is extended or adjusted under 35 U.S.C. 154(b) by 0 days.

(21) Appl. No.: 10/080,598

(22) Filed: Feb. 22, 2002

(51) Int. Cl.[7] ..... A01H 5/00
(52) U.S. Cl. ..... Plt./321

(58) Field of Search ..... Plt./327

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Dahlia plant named 'Karma Corona', characterized by its erect, straight and strong flowering stems; dark green foliage; early flowering; double inflorescence form; golden orange-colored ray florets; excellent garden performance; and excellent inflorescence longevity.

1 Drawing Sheet

BOTANICAL CLASSIFICATION/CULTIVAR DESIGNATION

*Dahlia hybrida* cultivar Karma Corona.

BACKGROUND OF THE INVENTION

The present Invention relates to a new and distinct cultivar of Dahlia plant, botanically known as *Dahlia hybrida* and hereinafter referred to by the name 'Karma Corona'.

The new Dahlia is a product of a planned breeding program conducted by the Inventor in Lisse, The Netherlands. The objective of the breeding program is to create new cut flower Dahlia cultivars with straight strong flowering stems, decorative inflorescence form, attractive ray floret colors, and good inflorescence longevity.

The new Dahlia originated from a cross pollination made by the Inventor in 1997 of the *Dahlia hybrida* Wittemans Best, not patented, as the female or seed parent with an unnamed proprietary *Dahlia hybrida* seedling selection, not patented, as the male or pollen parent. The new Dahlia was discovered and selected by the Inventor as a single flowering plant within the progeny of the stated cross grown in a controlled environment in Lisse, The Netherlands, in the summer of 1998. The selection of this plant was based on its strong straight stems and attractive ray floret coloration.

Asexual reproduction of the new Dahlia by cuttings was first conducted in Lisse, The Netherlands in the Spring of 1999. Asexual reproduction by cuttings has shown that the unique features of this new Dahlia are stable and reproduced true to type in successive generations.

SUMMARY OF THE INVENTION

The cultivar Karma Corona has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Karma Corona'. These characteristics in combination distinguish 'Karma Corona' as a new and distinct Dahlia cultivar:

1. Erect, straight and strong flowering stems.
2. Dark green foliage.

3. Early flowering response.
4. Double inflorescence form.
5. Golden orange-colored ray florets.
6. Excellent garden performance.
7. Excellent inflorescence longevity.

Plants of the new Dahlia are shorter, flower about two weeks earlier, and have longer lasting inflorescences than plants of the female parent, the cultivar Wittemans Best. In addition, plants of the new Dahlia have golden orange-colored ray florets whereas plants of the cultivar Wittemans Best have red-colored ray florets.

Plants of the new Dahlia differ primarily from plants of the male parent, an unnamed proprietary seedling selection, in ray floret coloration.

Plants of the new Dahlia can be compared to plants of the cultivar Gold Crown, not patented. In side-by-side comparisons conducted in Lisse, The Netherlands, plants of the new Dahlia have shorter, but stronger flowering stems than plants of the cultivar Gold Crown. In addition, inflorescences of plants of the new Dahlia have longer lasting inflorescences with darker colored ray florets than plants of the cultivar Gold Crown.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of a typical flowering stem of 'Karma Corona'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn of 2001 in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three weeks after planting rooted cuttings. Plants were about 100 days old when the photographs and the description were taken.

Botanical classification: *Dahlia hybrida* cultivar Karma Corona.

Parentage:

*Female, or seed, parent.*—*Dahlia hybrida* cultivar Witemans Best, not patented.

*Male, or pollen, parent.*—Unnamed proprietary *Dahlia hybrida* seedling selection, not patented.

Propagation:

*Type.*—By vegetative cuttings.

*Time to initiate roots.*—Summer: About 10 days at 18° C. Winter: About 12 days at 18° C.

*Time to develop roots.*—Summer: About 24 days at 18° C. Winter: About 27 days at 18° C.

*Root description.*—Fine, fibrous and well-branched; older roots, fleshy.

*Tuber description.*—Shape: Fusiform. Clump diameter: About 25 cm. Color: Close to 199C, with anthocyanin, 59C.

Plant description:

*Appearance.*—Perennial double-inflorescence type cut Dahlia. Erect, straight and strong flowering stems.

*Growth rate.*—Moderate; moderately vigorous.

*Crop time.*—After planting rooted cuttings, about 75 to 80 days are required to produce flowering stems.

*Plant height.*—About 110 cm.

*Plant diameter.*—About 40 cm.

*Flowering stem (peduncle) description.*—Quantity of flowering stems per plant: Pinched plants will develop 8 to 10 flowering stems. Length: About 70 cm. Diameter: Towards base: About 1.3 cm. Mid-section: About 9.5 mm. Towards apex: About 2 mm. Internode length: About 11 cm. Strength: Strong. Aspect: Erect, straight. Texture: Glabrous, smooth. Color: Towards base, 144B; towards apex, 144B overlain with anthocyanin, 187A. Lateral branches (peduncles): Quantity of lateral flowering branches per flowering stems: About four. Length: About 23 cm. Diameter: Towards base: About 9.5 mm. Towards apex: About 2 mm. Angle: About 80 to 90° from vertical. Strength: Strong. Aspect: Erect, straight. Texture: Glabrous, smooth. Color: Towards base, 144B; towards apex, 144B overlaid with anthocyanin, 187A.

*Foliage description.*—Arrangement: Leaves opposite; leaves may be single or compound with three or five leaflets. Shape: Ovate. Apex: Acuminate. Base: Attenuate. Margin: Irregularly serrate. Length: Single leaves: About 5 cm. Compound leaves with three leaflets: About 14 cm. Compound leaves with five leaflets: About 21 cm. Width: Single leaves: About 3.5 cm. Compound leaves with three leaflets: About 9 cm. Compound leaves with five leaflets: About 14 cm. Venation pattern: Pinnate. Texture: Smooth, glabrous; leathery. Color: Young foliage, upper surface: 146B. Young foliage, lower surface,: 147B. Fully developed foliage, upper surface: 147A. Fully developed foliage, lower surface: 147B. Venation, upper surface: 146D. Venation, lower surface: 146A. Petiole length: Single leaves: About 7 mm. Compound leaves: About 5 cm. Petiole diameter, single and compound leaves: About 3 mm. Petiole color: Upper surface: 143C overlaid with anthocyanin, 60A. Lower surface: Close to 160D.

Inflorescence description:

*Appearance.*—Double-type inflorescence form; dahlia cactus form. Inflorescences borne on terminals, arising from leaf axils. Ray and disc florets arranged acropetally on the receptacle. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 25 days in an outdoor environment. As cut flowers, inflorescences maintain good color and substance for about seven days in an indoor environment.

*Quantity of inflorescences per flowering stem.*—One per lateral stem; about three to four inflorescences per flowering stem; about 40 inflorescences per plant develop during the growing season, summer through autumn.

*Inflorescence size.*—Shape, in profile: Roughly hemispherical. Diameter: About 14 cm. Depth (height): About 10 cm. Diameter of disc: About 1.3 cm; inconspicuous. Receptacle diameter: About 2.2 cm. Receptacle height: About 4 mm.

*Inflorescence buds.*—Length: About 2.2 cm. Diameter: About 2.2 cm. Shape: Oblate to globular. Color: 151B.

*Ray florets.*—Length, fully developed: About 6.5 cm. Width, fully developed: About 1.5 cm. Orientation: Initially incurved to upright, outer florets perpendicular to peduncle to somewhat reflexed. Shape: Elongated oblong; convex. Apex: Acute. Base: Attenuate. Margin: Entire. Texture: Smooth, glabrous; satiny to slightly shiny. Number of ray florets per inflorescence: About 108 arranged in about 12 rows. Venation pattern: Parallel. Color: When opening, upper surface: 6A; longitudinal ridges, 61B. When opening, lower surface: 6A underlain with 61A. Fully opened, upper surface: Towards base, 7A; mid-section and towards apex, 7A overlaid with 63A; color fading to 169A with subsequent development. Fully opened, lower surface: Towards base, 8A; towards margin, 8A underlaid with 63A; lengthwise along the center, 8A underlaid with 64B.

*Disc floret.*—Number of disc florets per inflorescence: About 37. Shape: Tubular, elongated. Apex: Five-pointed. Base: Attenuate. Length: About 1.3 cm. Width: About 2 mm. Color: Immature: 7A. Mature: Apex: 21B. Mid-section: 23A. Base: Close to 1A.

*Phyllaries.*—Quantity: One whorl with about seven phyllaries. Shape: Ovate. Apex: Acute. Base: Attenuate. Margin: Entire. Length: About 2.1 cm. Width: About 1.7 cm. Texture: Smooth, glabrous. Color: Upper surface: 144A. Lower surface: 144A, overlaid with anthocyanin, 187A.

*Reproductive organs.*—Androecium: Present on disc florets only. Stamen quantity: About five per floret. Anther length: About 7 mm. Anther color: 16A. Pollen amount: Scarce. Pollen color: 21B. Gynoecium: Present on ray and disc florets. Pistil quantity: One per floret. Pistil length: About 3 mm. Stigma shape: Lanceolate. Stigma color: Close to 12B. Style length: About 3 mm. Style color: 150B. Ovary color: 8A.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Karma Corona' as illustrated and described.

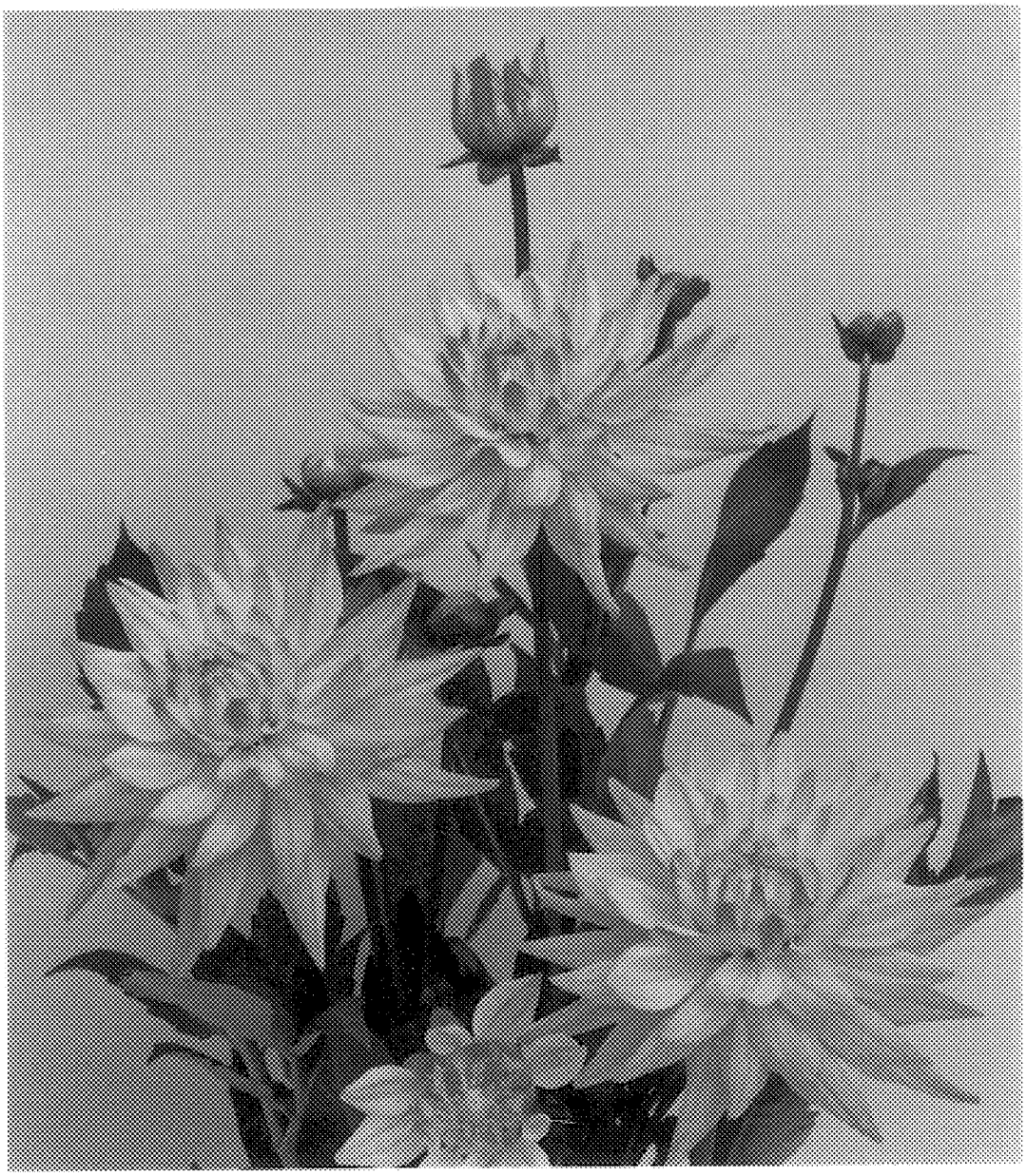

* * * * *